United States Patent [19]
Kanga et al.

[11] Patent Number: 5,695,772
[45] Date of Patent: Dec. 9, 1997

[54] COSMETIC COMPOSITIONS INCLUDING POLYISOBUTENE

[75] Inventors: Vispi Kanga, Shelton; Alexander Paul Znaiden, Trumbull, both of Conn.

[73] Assignee: Chesebrough-Pond's USA Co., Division of Conopco, Inc., Greenwich, Conn.

[21] Appl. No.: 703,764

[22] Filed: Aug. 27, 1996

[51] Int. Cl.⁶ ............................................. A61K 7/02
[52] U.S. Cl. ............................................. 424/401
[58] Field of Search ..................... 424/401, 78.03

[56] References Cited

U.S. PATENT DOCUMENTS

| | | |
|---|---|---|
| 4,806,572 | 2/1989 | Kellett . |
| 4,886,545 | 12/1989 | Peck et al. .................. 71/88 |
| 5,011,681 | 4/1991 | Ciotti et al. . |
| 5,160,739 | 11/1992 | Kanga . |
| 5,302,382 | 4/1994 | Kasprzak . |
| 5,306,838 | 4/1994 | Shioya et al. ............ 556/445 |
| 5,332,569 | 7/1994 | Wood et al. . |
| 5,340,570 | 8/1994 | Wong et al. . |
| 5,387,417 | 2/1995 | Rentsch . |
| 5,439,682 | 8/1995 | Wivell et al. . |
| 5,525,344 | 6/1996 | Wivell ...................... 424/401 |

OTHER PUBLICATIONS

Photocopy of Oil of Olay Moisturizing Body Wash Bottle—1992.
Photocopy of Ponds Cold Cream Water Rinsable Cleanser—1995.
Photocopy of Oil of Olay Water Rinsable Cold Cream—1995.

*Primary Examiner*—Thurman K. Page
*Assistant Examiner*—D. Faulkner
*Attorney, Agent, or Firm*—Milton L. Honig

[57] ABSTRACT

A cold cream cosmetic composition, preferably clear, is provided that includes water, a $C_2$–$C_6$ polyhydric alcohol, a hydrocarbon polymer formed from 6 to 1,000 repeating units of $C_4$–$C_{20}$ alkene monomer and a silicone emollient. These compositions exhibit visual clarity with excellent make-up and grime removal while being extremely low in their greasiness feel on skin.

4 Claims, No Drawings

COSMETIC COMPOSITIONS INCLUDING POLYISOBUTENE

BACKGROUND OF THE INVENTION

1. Field of the Invention

The invention concerns a non-classical cold cream cosmetic composition with improved make-up removal efficacy and a less greasy feel.

2. The Related Art

Modern cleansing creams are based on the solvent action of mineral oil to remove through binding either grime or make-up from skin. Removal of pigments of rouge, lipstick and face powder is a daily problem for most women. Cleansing creams have proved the ideal agent to perform this function.

Historically cleansing creams evolved over a period of centuries. Galen, a Greek physician around the year 150, is reported to be the inventor of the first cold cream. Skin preparations of that period consisted of animal and vegetable fats and oils. Beeswax and olive oil were the prime ingredients. Galen conceived the idea of incorporating water into a molten mixture of beeswax and olive oils. In the resultant product, the emollient effect of oil was accelerated, and a pleasant cooling effect was obtained from evaporation of water. Unfortunately the process of manufacture was slow and laborious. Products were also unstable and subject to developing rancidity. In time, sweet almond oil replaced the olive oil of the older formulations. Borax was introduced to cut manufacturing time, and a whiter and more stable emulsion resulted.

A cold cream can be classified as a form of cleansing cream but with a heavier body. These products were originally described as "refrigerans", latin for "making cold", because when applied they create a cooling sensation. Until early this century, many druggists would compound their own Ointment of Rose Water and keep it fresh on ice, hence, "cold" skin cream. The dictionary describes cold cream as a soothing and cleansing cosmetic or a cosmetic, typically of oily and heavy consistency, used to soothe and cleanse the skin. Classic cold cream is one containing the components beeswax, mineral oil, water and borax. Interest has arisen in non-classical forms of cold cream, especially those that combine enhanced aesthetics with efficacy.

U.S. Pat. No. 5,525,344 (Wivell) reports achieving a clear cold cream by combining water, a $C_2$–$C_6$ polyhydric alcohol, a poly($C_2$–$C_4$ alkoxylate) polymer, a volatile $C_{10}$–$C_{20}$ hydrocarbon and a silicone emollient. This product was said to exhibit visual clarity with excellent make-up and grease removal properties in addition to a superior, non-greasy feel. While this formulation significantly advanced the art, additional improvements are warranted especially with respect to reducing the products' greasy feel.

Accordingly, it is an object of the present invention to provide a cosmetic composition which exhibits less greasiness than prior similar products yet retains equivalent make-up removal and cleansing efficacy.

Another object of the present invention is to provide a cosmetic composition which is a clear (transparent) product retaining many of the physical attributes of traditional opaque cold creams.

Still another object of the present invention is to provide a cosmetic composition in the form of a clear cold cream which does not readily discolor upon prolonged exposure to light.

These and other objects of the present invention will become more readily apparent through the following summary and detailed description.

SUMMARY OF THE INVENTION

A cold cream cosmetic composition is provided that includes:

(i) from 1 to 50% by weight of water;

(ii) from 1 to 60% by weight of a $C_2$–$C_6$ polyhydric alcohol;

(iii) from 0.1 to 40% by weight of a hydrocarbon polymer formed from 6 to 1,000 repeating units of a $C_4$–$C_{20}$ alkene monomer; and (iv) from 0.1 to 30% by weight of a silicone emollient.

DETAILED DESCRIPTION OF THE INVENTION

It has been discovered that a cold cream composition with excellent make-up removability but with much less greasiness of feel can be achieved by combining a hydrocarbon polymer in an aqueous emulsion with a $C_2$–$C_6$ polyhydric alcohol and a silicone emollient. In particular, compositions of the present invention are water-in-oil emulsions, with the external oil phase operating to achieve the cold cream cleansing effect for make-up removal. The oil phase should preferably constitute from 5 to less than 50%, more preferably 10 to 30%, optimally from 12 to 18% by weight of the total composition. Thickening and transparency is achieved by utilizing a high level of internal aqueous phase. Amounts of the aqueous phase will be at least 50%, preferably between 70 and 90% by weight of the composition.

Compositions of the present invention are intended to be optically clear cosmetic products with the ability to be packaged in a clear container. These compositions are intended to preferably have a refractive index of 1.3975 to 1.4200 at 21° C., an optical clarity better than 50 NTU (Nephelometric Turbidity Units) at 21° C. and a viscosity of at least 10,000 cps, preferably at least 30,000 cps at 21° C. The refractive indices (measured at 5891° A) of the water and oil phases should match within 0.0050, preferably within 0.004 refractive index units. An optically clear cold cream of the present invention should be one that is visually clear, and, like glass, allows ready viewing of objects behind it. Preferably, the compositions will have a turbidity measurement of less than 30 NTU. Distilled water has a turbidity of 0 NTU and whole milk diluted 1 part in 350 parts of distilled water has a turbidity of 200 NTU.

Water is an essential element of the aqueous phase of compositions according to the present invention. Amounts of water may range from 1 to 50%, preferably from 10 to 35%, optimally from 15 to 30% by weight.

Another component of the aqueous phase of compositions according to the present invention is a polyhydric alcohol containing from 2 to 6 hydroxyl groups, preferably from 2 to 3 hydroxyl groups. The alcohol may also contain from 2 to 6 carbon atoms, preferably from 2 to 4 carbon atoms. Suitable polyhydric alcohols include ethylene glycol, propylene glycol, trimethylene glycol, 1,3-butylene glycol, isoprene glycol, glycerin and sorbitol. Most preferred is a combination of 1,3-butylene glycol and isoprene glycol (CTFA name: Isopentyldiol), the latter available from the Kuraray Company, Ltd., Tokyo, Japan. Relative ratios of 1,3-butylene glycol and isoprene glycol may range from 20:1 to 1:20, preferably from 10:1 to 1:2, optimally from 4:1 to 1:1 by weight. Amounts of the polyhydric alcohol may range from 1 to 60%, preferably from 10 to 50%, optimally from 25 to 35% by weight of the total composition. Glycerin and diglycerin, especially in ratios of 2:1 to 1:2, preferably 1:1, can also be present.

An essential element of compositions according to the present invention is that of a hydrocarbon polymer formed from 6 to 1,000 repeating units of a $C_4$-$C_{20}$ alkene monomer. Especially preferred are per-alk(en)yl hydrocarbon materials of the formula:

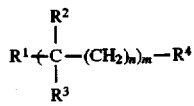

wherein:

n is an integer from 0 to 3, preferably 1;

m is an integer such that the weight average molecular weight of the hydrocarbon will range from 300 to 50,000, preferaby from 500 to 5,000;

$R^1$ is —H or a $C_{1-4}$ alkyl group; preferably methyl;

$R^2$ is a $C_{1-4}$ alkyl group; preferably methyl;

$R^3$ is —H or a $C_{1-4}$ alkyl group; preferably —H or methyl

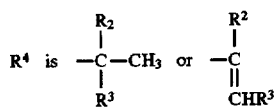

Especially preferred are polyisobutene materials of the formula:

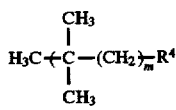

wherein $R^4$ is

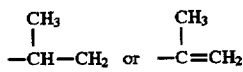

The hydrocarbon polymer of choice is Panalane L-14 E, a material sold commercially by the Amoco Chemical Company, Chicago, Illinois. The CTFA (Cosmetic, Toiletry and Fragrance Association) has identified this material as Hydrogenated Polyisobutene.

Amounts of the hydrocarbon polymer generally range from 0.1 to 40%, preferably from 1 to 20%, optimally from 3 to 8% by weight.

An optional further component of the aqueous phase of compositions according to the present invention is that of a poly ($C_2$-$C_4$ alkoxylate) polymer. This polymer will contain from 3 to 200 units of $C_2$-$C_4$ alkylene oxide monomer units. These units may either be homopolymerized, copolymerized with another alkylene oxide monomer unit, or condensed with an organic hydrophobe such as a $C_2$-$C_{20}$ alkanoic acid or alcohol. Illustrative homo-and copolymers are polyethylene glycol, polypropylene glycol and poly(ethylene oxide) (propylene oxide), commercially available from the BASF Corporation under the Pluronic trademark. Illustrative of those with hydrophobe units are PPG-15 stearyl ether, PEG-10 stearyl ether, PPG-15 palmityl ether and Poloxamine 1307 (commercially available from the BASF Corporation under the Tetronic® 1307 trademark). Most preferred is polyethylene glycol, especially PEG-5, PEG-32, PEG-400 and combinations thereof. Amounts of the poly ($C_2$-$C_4$ alkoxylate) polymer can range from 1 to 50%, preferably from 10 to 30%, optimally from 15 to 25% by weight of the total composition.

Preservatives can also be incorporated in amounts effective to protect against growth of potentially harmful microorganism in cosmetic compositions acccording to the present invention. Preferably they are added to the aqueous phase, but some may be added to the oil phase. Levels of such preservatives may range from 0.001 to 1% by weight. Illustrative preservatives are methyl paraben, propyl paraben, imidazolidinyl urea, sodium dehydroxyacetate and benzyl alcohol. Other minor adjunct ingredients may also be included such as fragrances, electrolytes and colorants, each in their effective amounts to accomplish their respective functions.

The oil phase of emulsion compositions according to the present invention will ordinarily comprise a mixture of the hydrocarbon polymer and silicone emollients.

Silicone oils will constitute from 0.1 to 30%, preferably from 1 to 20%, optimally from 5 to 15% by weight of the total composition. These silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. The linear types are known by the CTFA name of dimethicone while the cyclic types are known by the CTFA name of cyclomethicone. The cyclomethicones are commercially available from Dow Corning under the trademark DC 344 and DC 345.

Nonvolatile silicone oils useful in composition of the present invention are exemplified by the polyalkyl siloxanes, polyalkylaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Preferred polydimethyl siloxanes are those having viscosities from 10 to 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from 15 to 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of 1,200 to 1,500 centistokes at 25° C. Such a fluid is available as SF-1066 organosilicone surfactant (sold by General Electric Company).

For purposes of this invention, most advantageous is the use of a combination of cyclomethicone, dimethicone copolyol and dimethiconol. In particular, it is desirable to use a combination of Dow Corning 3225C and Dow Corning 1401. Dow Corning 3225C is a mixture of cyclomethicone-dimethicone copolyol silicone fluid having a viscosity at 25° C. of 100-1,000 cst and a specific gravity at 25° C. of about 0.963. Amounts of this particular silicone may be present from 1 to 10% of the total composition. Dow Corning 1401 is a blend of cyclomethicone and dimethiconol having a viscosity at 25° C. of 5,000–7,000 cst and a specific gravity at 25° C. of 0.960. Amounts of Dow Corning 1401 may range from 0.5 to 10%, preferably from 2 to 6% by weight of the total composition.

Synthetic and natural ester emollients may also be included in the compositions. Most preferred are the tri ($C_2$–$C_{12}$ alkyl) esters of citric acid, most preferably tributyl citrate. Amounts may range from 0.001 to 1%, preferably from 0.01 to 0.5% by weight.

Maintenance of a good color within a clear variety of the cold cream may be maintained by incorporating relatively small levels of a UV absorber. UVA and/or UVB wavelength absorbers may be utilized. Most preferred is butyl methoxydibenzoylmethane, available as Parsol® 1789.

A variety of surfactants may be incorporated in the compositions. Most preferred are the $C_6$–$C_{20}$ alkyl polyglycosides such as decyl polyglucose (CTFA nomenclature), available as Plantareen 2000® from the Henkel Corporation of Ambler, Pa.

The following examples will more fully illustrate select embodiments of this invention. All parts, percentages and proportions referred to herein and in the appended claims are by weight unless otherwise indicated.

EXAMPLES 1–5

Illustrative of the present invention are a series of clear cold creams as outlined under Table I.

TABLE I

| TRADENAME | CHEMICAL NAME/ CTFA NAME | EXAMPLES | | | | |
|---|---|---|---|---|---|---|
| | | 1 | 2 | 3 | 4 | 5 |
| Butylene Glycol | 1,3-Butylene Glycol | 20.00 | 15.00 | 15.00 | 10.00 | 10.00 |
| PEG 540 Blend | PEG-6 and PEG-32 | 10.00 | 15.00 | 10.00 | 20.00 | 15.00 |
| Sodium Chloride | Sodium Chloride | 5.00 | 5.00 | 3.00 | 2.00 | 5.00 |
| Glycerin | Glycerin | 4.00 | 4.00 | 5.00 | 5.00 | 3.00 |
| Diglycerin | Diglycerol | 4.00 | 4.00 | 5.00 | 5.00 | 3.00 |
| Isoprene Glycol | Isopentyldiol | 3.00 | 3.00 | 5.00 | 5.00 | 3.00 |
| Plantaren 2000 | Decyl Polyglucose | 3.00 | 3.00 | 4.00 | 4.00 | 4.00 |
| Benzyl Alcohol | Benzyl Alcohol | 0.50 | 0.50 | 0.50 | 0.50 | 0.50 |
| DL Panthenol | DL Panthenol | 0.01 | 0.01 | 0.01 | 0.01 | 0.01 |
| Glycolic Acid-70 | Glycolic Acid | 0.01 | 0.01 | 0.01 | 0.01 | 0.01 |
| Phenonip | Phenoxyethanol & 4 Parabens | 0.20 | 0.20 | 0.20 | 0.20 | 0.20 |
| Violet #2 (0.20%) | Color | 0.03 | 0.03 | 0.03 | 0.03 | 0.03 |
| Witch Hazel | Witch Hazel Extract | 0.20 | 0.20 | 0.20 | 0.20 | 0.20 |
| Water, Deionized | Water | bal. | bal. | bal. | bal. | bal. |
| OIL PHASE | | | | | | |
| Panalane L-14E | Hydrogenated Polyisobutenes | 10.00 | 6.00 | 4.00 | 2.00 | 1.00 |
| Permethyl 99A | Isododecane | 2.00 | 2.00 | 1.00 | 1.00 | 1.00 |
| Stabilizer 89 | Butyl Methoxydibenzoylmethane | 0.03 | 0.03 | 0.03 | 0.03 | 0.03 |
| Dermol Cl | Cetyl Lactate | 0.01 | 0.01 | 0.01 | 0.01 | 0.01 |
| Tributyl Citrate | Tributyl Citrate | 0.01 | 0.01 | 0.01 | 0.01 | 0.01 |
| Vitamin E USP | Vitamin E Acetate | 0.01 | 0.01 | 0.01 | 0.01 | 0.01 |
| DC 1401 Fluid | Cyclomethicone (&) Dimethiconol | 12.00 | 12.00 | 8.00 | 8.00 | 4.00 |
| DC 3225C | Cyclomethicone (&) Dimethicone Copolyol | 4.00 | 4.00 | 8.00 | 6.00 | 4.00 |
| DC 344 Fluid | Cyclomethicone | 0.80 | 0.80 | 0.80 | 0.80 | 0.80 |
| Fragrance | Fragrance | 0.14 | 0.14 | 0.14 | 0.14 | 0.14 |

EXAMPLE 6

This Example details the effectiveness of formulations with polyisobutene for make-up removal and their relatively low level of greasiness compared to identical formulations with isohexadecane or isododecane. Table II lists the formulations tested.

TABLE II

| INGREDIENTS | COLD CREAM % W/W A | COLD CREAM % W/W B | COLD CREAM % W/W C | COLD CREAM % W/W D |
|---|---|---|---|---|
| Butylene Glycol-1,3 | 15.000 | 15.000 | 15.000 | 15.000 |
| PEG 540 Blend | 10.000 | 10.000 | 10.000 | 10.000 |
| Glycerin | 5.000 | 5.000 | 5.000 | 5.000 |
| Isoprene Glycol | 5.000 | 5.000 | 5.000 | 5.000 |
| Diglycerin | 5.000 | 5.000 | 5.000 | 5.000 |
| Plantaren 2000 | 4.000 | 4.000 | 4.000 | 4.000 |
| Sodium Chloride | 3.000 | 3.000 | 3.000 | 3.000 |
| Benzyl Alcohol | 0.500 | 0.500 | 0.500 | 0.500 |
| Phenonip | 0.200 | 0.200 | 0.200 | 0.200 |
| Water | 30.370 | 30.370 | 34.370 | 35.370 |
| OIL PHASE | | | | |
| DC 344 Fluid | 0.900 | 0.900 | 0.900 | 0.900 |
| DC 3225 C | 8.000 | 8.000 | 8.000 | 8.000 |
| DC 1401 Fluid | 8.000 | 8.000 | 8.000 | 8.000 |
| Panalane L-14E (Polyisobutene) | 4.000 | — | — | — |
| Permethyl 99 A (Isododecane) | — | — | 4.000 | — |
| Permethyl 101A (Isohexadecane) | — | 4.000 | — | — |
| Parsol 1789 | 0.030 | 0.030 | 0.030 | 0.030 |

Greasiness/Rinse-Off Evaluation

Cold Creams A–D were provided to five subjects on a blind basis. Each subject was asked to evaluate the four products on two skinfeel properties. These properties were: (1) Is not greasy or oily; (2) Rinses off and doesn't leave a residue on the skin. The rating system was from 1 to 4, respectively indicating very good, good, fair and poor.

Formula A with polyisobutene was similar to the control (Formula D) in being less greasy, easy to rinse off and left least residue on the skin. Two subjects indicated that the polyisobutene formula was the easiest to rinse-off. All five subjects perceived the isohexadecane (Formula B) and isododecane (Formula C) as greasier than the control (Formula D). Three of the five subjects were unable to distinguish differences between isohexadecane and isododecane formulas in their level of greasiness. Two subjects indicated that the isohexadecane formula was more greasy than the isododecane formula.

Make-Up Removal Evaluation

Make-up removal was performed using the following two mascaras:

(1) Elizabeth Arden® Two Brush Waterproof Mascara
(2) Maybelline® Ultra-Big Ultra Lash Mascara Both of the aforementioned mascaras were chosen because they are very substantive, waterproof and difficult to remove compared to conventional make-ups. Table III reports the preferences of the five subject panel.

TABLE III

| REMOVES MASCARA EASILY | | VERY GOOD | GOOD | FAIR | POOR |
|---|---|---|---|---|---|
| Cold Cream A: | Arden | 4 | 1 | 0 | 0 |
| | Maybelline | 5 | 0 | 0 | 0 |
| Cold Cream B: | Arden | 1 | 4 | 0 | 0 |
| | Maybelline | 1 | 4 | 0 | 0 |

TABLE III-continued

| REMOVES MASCARA EASILY | VERY GOOD | GOOD | FAIR | POOR |
|---|---|---|---|---|
| Cold Cream C: Arden | 1 | 4 | 0 | 0 |
| Maybelline | 5 | 0 | 0 | 0 |
| Cold Cream D: Arden | 0 | 0 | 0 | 5 |
| Maybelline | 0 | 0 | 1 | 4 |

From Table III it can be concluded that the control product (Cold Cream D) was inefficient in removing make-up. By contrast, the polyisobutene containing Cold Cream A as well as the isohexadecane and isododecane formulas were well able to remove waterproof mascara.

The foregoing description and Examples illustrate selected embodiments of the present invention. In light thereof, various modifications will be suggested to one skilled in the art, all of which are within the spirit and purview of this invention.

What is claimed is:

1. A cold cream cosmetic composition comprising:
   (i) from 1 to 50% by weight of water;
   (ii) from 10 to 60% by weight of a $C_2$–$C_6$ polyhydric alcohol;
   (iii) from 1 to 20% by weight of a polyisobutene; and
   (iv) from 1 to 30% by weight of a silicone emollient.

2. The composition according to claim 1 wherein the polyol is a mixture of 1,3-butylene glycol and isoprene glycol in a weight ratio ranging from 10:1 to 1:10.

3. The composition according to claim 1 wherein the silicone emollient is a cyclomethicone-dimethicone copolyol silicone fluid mixture having a viscosity of 25° C. of 100 to 1,000 cSt.

4. The composition according to claim 1 which is a water-in-oil emulsion with an aqueous phase from 70 to 90% and an oil phase from 5 to less 50% by weight of the total composition.

* * * * *